United States Patent [19]

Cullen et al.

[11] Patent Number: 4,975,451
[45] Date of Patent: Dec. 4, 1990

[54] INSECTICIDAL CYCLOPROPYL DI(ARYL) 2-BUTENES

[75] Inventors: Thomas G. Cullen, Milltown, N.J.; Scott McN. Sieburth, East Windsor, N.J.; Gary A. Meier, Robbinsville, N.J.; John F. Engel, Washington Crossing, Pa.; Leslie W. Stratton, Trenton; Alan W. Fritz, Kendall Park, both of N.J.

[73] Assignee: FMC Corporation, Philadelphia, Pa.

[21] Appl. No.: 318,230

[22] Filed: Mar. 2, 1989

[51] Int. Cl.$^5$ .................... C07C 43/20; A01N 31/08
[52] U.S. Cl. .................... 514/432; 549/15; 549/16; 549/17; 549/23; 549/26; 549/31; 549/32; 549/35; 549/43; 549/50; 549/58; 549/66; 549/78; 549/359; 549/362; 549/389; 549/407; 549/433; 549/434; 549/458; 549/462; 568/632; 568/635
[58] Field of Search .................... 568/635; 549/66, 78, 549/15, 16, 17, 23, 26, 31, 32, 43, 35, 49, 59, 362, 389, 396, 434, 443, 460, 469, 435, 50, 58, 407, 433, 458, 462; 514/717, 438, 432, 434, 437, 438, 440, 443, 444, 454, 456, 463, 464, 465, 468, 469, 452

[56] References Cited

U.S. PATENT DOCUMENTS

| | | | |
|---|---|---|---|
| 4,153,731 | 5/1979 | Karrer | 424/337 |
| 4,575,517 | 3/1986 | Kruger et al. | 514/715 |
| 4,611,004 | 9/1986 | Ackermann et al. | 514/164 |

FOREIGN PATENT DOCUMENTS

| | | | |
|---|---|---|---|
| 0193189 | 9/1986 | European Pat. Off. | 568/635 |
| 118534 | 7/1983 | Japan | 568/635 |
| 109505 | 6/1985 | Japan | 568/635 |
| WO85/04651 | 10/1988 | PCT Int'l Appl. | 514/464 |
| WO88/08416 | 11/1988 | PCT Int'l Appl. | 514/464 |
| 2085006 | 4/1982 | United Kingdom | 514/464 |
| 2120664 | 12/1983 | United Kingdom | 568/635 |

OTHER PUBLICATIONS

Udagawa et al., "A New Type of Synthetic Pyrethroid Insecticide", Recent.
Nakatani et al., Mitsui Toatsu Chemicals, Inc., Chemical Abstracts No. 104: 125070v.
Sumitomo Chemical Co., Ltd., Chemical Abstract No. 103:214976s, 25-Benzenes, vol. 103, p. 214988, 1985.
Elliott et al., National Research Development Corp., Chemical Abstract No. 104: 129539c.
Udagawa et al., Mitsui Toatsu Chemicals, Inc., Chemical Abstract No. 104: 163745b, 5-Agrochemicals, vol. 104, p. 235, 1986.
Udagawa et al., Mitsui Toatsu Chemicals, Inc., Chemical Abstract No.: 106: 133827d, 5-Agrochemicals, vol. 106, p. 217, 1987.
Hirano et al., Sumitomo Chemical Co., Ltd., Chemical Abstract No.: 104: 143987d, vol. 104, p. 244, 1986.
Kawai, Mitsui Toatsu Chemicals, Inc., Chemical Abstract No. 106: 68281e.
Franke et al., Schering A-G, Chemical Abstract No. 106: 32527a, vol. 106, p. 500, 1987.
Numata et al., Mitsui Toatsu Chemicals, Inc., Chemical Abstract No.: 106: 32559n, vol. 106, p. 502, 1987.
Nishimura, et al., "Symptomatic and Neurophysiological Activities of New Synthetic Non-ester Pyrethroids, Ethofenprox, MTI-800, and Related Compounds", Pesticide Biochemistry and Physiology, 25, 387-395, (1986).
Nakatani et al., Chemical Abstracts No. 100: 174420K, vol. 100, p. 594, 1984.
Mitsui Toatsu Chemicals, Inc., Chemical Abstracts No. 103: 104696t, vol. 103, p. 596, 1985.
Mitsui Toatsu Chemicals, Inc., Chemical Abstracts No. 103: 191480j, 5-Agrochemicals, vol. 103, p. 191494, 1985.
Mitsui Toatsu Chemicals, Inc., Chemical Abstracts No. 103: 191481K, 5-Agrochemicals, vol. 103, p. 191494, 1985.
Sumitomo Chemical Co., Ltd., Chemical Abstracts No. 103: 214964m, 25-Benzenes, vol. 103, p. 214964, 1985.
Sumitomo Chemical Co., Ltd., Chemical Abstracts No. 103: 214969s, vol. 103, p. 863, 1985.
Sumitomo Chemical Co., Ltd., Chemical Abstracts No. 103: 214973p, vol. 103, p. 862, 1985.
Tsushima et al., Sumitomo Chemical Co., Ltd., Chemical Abstracts No. 104: 2226t, vol. 104, p. 204, 1986.

Primary Examiner—Robert W. Ramsuer
Assistant Examiner—Zinna Northington-Davis
Attorney, Agent, or Firm—Beverly K. Johnson; Robert M. Kennedy; H. Robinson Ertelt

[57] ABSTRACT

Compounds of the formula

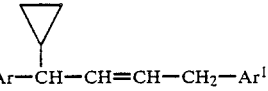

in which Ar is substituted or unsubstituted phenyl, naphthyl, or thienyl; and Ar$^1$ is 3-phenoxyphenyl, 4-fluoro-3-phenoxyphenyl, 2-methyl[1-1'-biphenyl]-3-yl, or 6-phenoxy-2-pyridyl, exhibit pyrethroid-like insecticidal and acaricidal activity and are relatively nontoxic to fish.

11 Claims, No Drawings

INSECTICIDAL CYCLOPROPYL DI(ARYL) 2-BUTENES

This invention pertains to novel pyrethroid-like, 2-butene derivatives, insecticidal and acaricidal compositions containing the derivatives as an active ingredient, and processes for the use thereof to control a variety of insects and acarids.

Synthetic pyrethroids have been the focus of intensive research activity for more than a decade. The vast majority of these pyrethroids have been esters of substituted cyclopropanecarboxylic acids similar to those described by Elliott in U.S. Pat. No. 4,024,163. Initially, compounds having the aforementioned structure were thought to be required for insecticidal activity. However, successful research efforts have defined compounds which are nominally described as pyrethroids based upon similarities in molecular geometry and insecticidal activity. In some of these new compounds only the ester linkage has been retained; and in yet others neither the substituted cyclopropane ring nor the ester linkage has been retained.

In the present invention, an unsubstituted cyclopropane group is incorporated into di(aryl)-2-butene compounds. The novel compounds lack the substituted cyclopropanecarboxylic acid moiety typical of the compounds described by Elliott and those who followed him. Further, these compounds display pyrethroid-like insecticidal activity while possessing remarkably low toxicity to fish in comparison with the notorious toxicity to fish exhibited by cyclopropanecarboxylates.

DESCRIPTION OF RELATED ART

PCT Application No. WO88/084160, published Nov. 30, 1988, discloses phenoxybenzyl pyrethroid-like compounds of the formula:

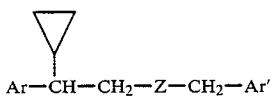

in which Ar is substituted or unsubstituted phenyl, naphthyl, or thienyl; Z is oxygen, sulfur, or methylene; and Ar' is 2-methyl[1,1'-biphenyl]-3-yl, 3-phenoxyphenyl, 4-fluoro-3-phenoxyphenyl, or 6-phenoxy-2-pyridyl exhibit pyrethroid-like insecticidal and acaricidal activity and are relatively harmless to aquatic fauna.

U.S. Pat. No. 4,397,864 discloses a class of pyrethroid-like compounds having the following subgeneric formula:

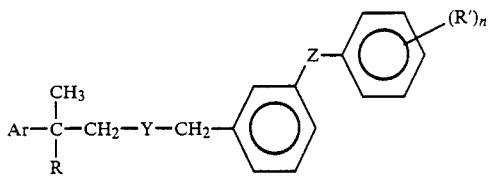

wherein
Ar is optionally substituted phenyl, optionally substituted naphthyl, or 1,3-benzodioxol-5-yl;
R is lower alkyl;
Y is O or S;
Z is O, S, or a carbonyl or methylene group.
R' is H, F, lower alkyl, or lower alkoxy; and
n is 1–5.

These compounds are alleged to have high insecticidal activity and low toxicity to fish.

U.S. Pat. No. 4,073,812 covers a closely related series of compounds having the generic formula:

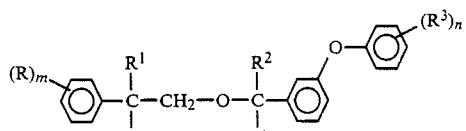

wherein
R is halogen, lower alkyl, or lower alkoxy;
m is 1 or 2;
$R^1$ is branched chain alkyl of 3–6 carbon atoms;
$R^2$ is hydrogen or alkynyl of 2–4 carbon atoms;
$R^3$ is fluorine; and
n is 0 or 1.

In all examples $R^1$ is isopropyl. All compounds are asserted to be insecticidal, some more than others, but there is no indication or assertion about the degree of toxicity to fish.

U.S. Pat. No. 4,562,213 covers another similar series of compounds of the formula:

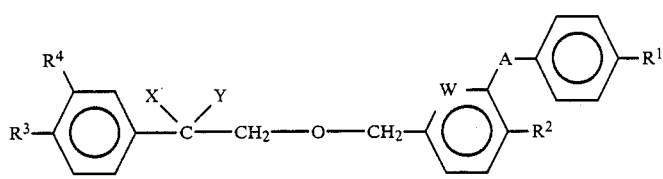

wherein
$R^1$ is hydrogen, halogen, or methyl;
$R^2$ is hydrogen or fluorine;
W is CH or N;
A is oxygen, methylene, or imino;
X and Y are both methyl or taken together form an optionally substituted cyclopropane ring;
$R^3$ and $R^4$ may be the same or different and are hydrogen, halogen, lower alkyl, lower alkoxy, lower fluoroalkoxy, or taken together form a methylenedioxy bridge.

In all cases where A is oxygen, X and Y are taken together to form a cyclopropane ring or a substituted cyclopropane ring. These compounds are asserted to be insecticidal and acaricidal without any assertion relating to fish toxicity.

United Kingdom patent application GB 2 120 664A discloses a class of aromatic-substituted alkane derivatives having the following generic formula:

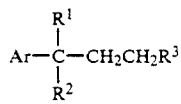

wherein

Ar stands for a substituted or unsubstituted phenyl or naphthyl group;

$R^1$ stands for a methyl, ethyl, or isopropyl group and $R^2$ stands for a hydrogen atom or a methyl group or $R^1$ and $R^2$ taken together with the carbon to which they are attached represent a substituted or unsubstituted cycloalkyl group; and $R^3$ stands for the residue of an alcohol, $R^3OH$, commonly found in natural or synthetic pyrethroids.

Examples of substituted or unsubstituted cycloalkyl groups named or exemplified by taking $R^1$ and $R^2$ together with the carbon to which they are attached are cyclopropyl, 2,2-dichlorocyclopropyl, cyclobutyl, cyclopentyl, and cyclohexyl. These compounds are asserted to be highly insecticidal and acaricidal and to have low toxicity to mammals and fish. Belgian patent No. 902147 discloses a class of compounds having the following generic formula:

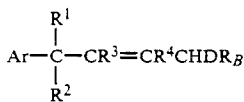

wherein

Ar represents a substituted or unsubstituted phenyl or naphthyl group;

$R^1$ and $R^2$ taken together with the carbon atom to which they are attached represent a substituted or unsubstituted cycloalkyl group of 3-6 carbon atoms;

$R^3$ and $R^4$, which may be the same or different, are hydrogen, halogen, or $C_1$-$C_6$ alkyl;

$R_B$ represents the residue of an alcohol, $R_BCHDOH$, which provides significant insecticidal activity when esterified with 1R,cis-3-(2,2-2-di thylcyclopropanecarboxylic acid; and D is hydrogen or cyano.

SUMMARY OF THE INVENTION

The compounds of this invention may be described as 1-cyclopropyl-1-(optionally substituted aryl)-4-(substituted aryl)-2-butenes. These compounds contain an asymmetric carbon atom and a carbon to carbon double bond; the invention thus includes individual stereoisomers as well as racemic and non-racemic mixtures of enantiomers of the instant compounds.

This invention also encompasses insecticidal compositions containing the compounds of this invention and the use thereof for controlling insects. The invention compounds are effective for control of a wide variety of insects and acarids and are expected to be useful in any situation in which pyrethroid insecticidal control is desired. A particularly useful advantage of the pyrethroid-like compounds of this invention lies in their low toxicity to fish. Application of the novel compounds in situations where there exist risks of significant contamination of streams, rivers and lakes, greatly reduces ecological concerns usually associated with the use of pyrethroids in these environments.

DETAILED DESCRIPTION

The 1-cyclopropyl-1-(optionally substituted aryl)-4-(substituted aryl)-2-butenes have the general formula:

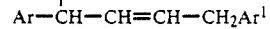

in which Ar is a substituted or unsubstituted phenyl, naphthyl, or thienyl. A substituted Ar may have one or two, not necessarily identical, substituents. Preferably Ar is phenyl and is monosubstituted at the 4-position. Preferred substituents include, but are not limited to, $(C_{1-6})$alkyl, halogen, $(C_{1-4})$haloalkyl, $(C_{1-4})$alkoxy, $(C_{1-4})$haloalkoxy. Further, the substituent may have the structure $-A-[C(R^1)(R^2)]_n-A-$ where $R^1$ and $R^2$ are independently, hydrogen, halogen, or alkyl having 1 to 2 carbon atoms, n is 1 or 2, and each A, which may be O, S, or $CH_2$, is bonded to a carbon atom of the Ar aromatic ring, wherein the carbons to which the A groups are attached are adjacent to each other in the ring. Illustrative of this mode of substitution are compounds in which Ar is 1,3-benzodioxolyl, 2,2-difluoro-1,3-benzodioxolyl, or 2,3-dihydro-2,2-dimethylbenzofuranyl. Typical Ar groups include:

phenyl, fluorophenyl, chlorophenyl, bromophenyl, preferably, 4-chlorophenyl;

methylphenyl, ethylphenyl, propylphenyl, isopropylphenyl, butylphenyl, isobutylphenyl, sec-butylphenyl, tert-butylphenyl, preferably methylphenyl;

methoxyphenyl, ethoxyphenyl, propoxyphenyl, isopropoxyphenyl, butoxyphenyl, isobutoxyphenyl, sec-butoxyphenyl, tert-butoxyphenyl, or cyclopropylmethoxyphenyl, preferably methoxyphenyl or ethoxyphenyl;

fluoromethylphenyl, chloromethylphenyl, trifluoromethylphenyl, difluoromethylphenyl, fluoroethylphenyl, chloroethylphenyl, preferably trifluoromethylphenyl;

difluoromethoxyphenyl, trifluoromethoxyphenyl, 2-fluoroethoxyphenyl, 1,1,2,2-tetrafluoroethoxyphenyl, 2-bromo-1,1,2,2-tetrafluoroethoxyphenyl, preferably trifluoromethoxyphenyl or difluoromethoxyphenyl;

1,3-benzodioxol-5-yl, 2,2-difluoro-1,3-benzodioxol-5-yl, naphthyl, thienyl, 2,3-dihydro-2,2-dimethylbenzofuran-5-yl, 2,2,3,3-tetrafluorobenzofuran-5-yl, and 2,3-dihydro-2,2-dimethylbenzofuran-7-yl; and $Ar^1$ is 2-methyl[1,1'-biphenyl]-3-yl, 3-phenoxyphenyl, 4-fluoro-3-phenoxyphenyl, and 6-phenoxy-2-pyridyl, preferably 4-fluoro-3-phenoxyphenyl. Substitution of the phenyl, pyridyl, or phenoxy moieties with halogen or alkyl is within the scope of this invention.

In a preferred embodiment, Ar is a phenyl group substituted in the 4-position with chloro, trifluoromethyl, or trifluoromethoxy; and $Ar^1$ is 3-phenoxyphenyl or 4-fluoro-3-phenoxyphenyl.

For purposes of this invention, the term alkyl is a straight chain, branched chain, and cyclic lower alkyl group having 1-6 carbon atoms, preferably 1-4 carbon atoms. The term halogen includes fluorine, chloride or bromine atoms. The terms haloalkyl and haloalkoxy include alkyl and alkoxy groups in which one or more hydrogen atoms have been replaced by fluorine, chlorine, or bromine atoms including all combinations thereof.

The compounds of this invention may be prepared by the use of steps generally described in the literature or by methods analogous or similar thereto and within the skill of the art.

The invention compounds may be prepared by reacting a cyclopropyl (optionally substituted)aryl ketone with vinylmagnesium bromide to prepare the corresponding 1-cyclopropyl-1-(optionally substituted aryl)-2-propen-1-ol. Reaction of the unsaturated alcohol with thionyl chloride and pyridine yields 3-chloro-1-cyclopropyl-1-(optionally substituted aryl)-1-propene which, in turn, can be converted to the corresponding triphenylphosphonium chloride by reaction with triphenylphosphine. Reaction of this phosphonium salt with the sodium salt of dimethyl sulfoxide and then with the appropriately substituted arylaldehyde yields the corresponding 1-cyclopropyl-1-(optionally substituted aryl)-4-(substituted aryl)-1,3-butadiene. The 1,3-butadiene compound may be reduced with magnesium, using a method analogous to that described by Proffit and Watt in J. Org. Chem., 40, 127 (1975), to yield the corresponding 1-cyclopropyl-1-(optionally substituted aryl)-4-(substituted aryl)-2-butene. Example 1 details the synthesis of 1-cyclopropyl-1-(4-trifluoromethoxyphenyl)-4-(4-fluoro-3-phenoxyphenyl)-2-butene, Compound 6 of Table 1, using this method.

Alternatively, the unsaturated, hydrocarbon compounds may be synthesized by oxidation of the 1-cyclopropyl-1-(optionally substituted aryl)-2-propen-1-ol, prepared as described above, to yield the corresponding 3-cyclopropyl-3-(optionally substituted aryl)propenal. Reaction of the (substituted) aralkyl halide with triphenylphosphine yields the corresponding (substituted) aralkyltriphenylphosphonium halide. The halide salt is then reacted with the 3-cyclopropyl-3(optionally substituted aryl)propenal in the presence of n-butyllithium to yield the 1-cyclopropyl-1-(optionally substituted aryl)-4-(substituted aryl)-1,3-butadiene which, in turn, may be reduced as described above to yield the desired 1-cyclopropyl-1-(optionally substituted aryl)-4-(substituted aryl)-2-butene. Example 2 details the preparation of 1-cyclopropyl-1-(4-chlorophenyl)-4-(4-fluoro-3-phenoxyphenyl)-2-butene, Compound 2, using this synthesis.

Certain of the starting aryl cyclopropyl ketones, e.g., 4-chlorophenyl cyclopropyl ketone, are commercially available. Others can be synthesized by reacting an appropriately substituted benzonitrile with cyclopropylmagnesium bromide. Example 1, Step A, is representative of this method and provides details for the synthesis of 4-trifluoromethoxyphenyl cyclopropyl ketone.

Alternatively, the aryl cyclopropyl ketones may be prepared by converting an appropriately substituted benzoic acid to the acid chloride by usual methods, e.g., by reaction with oxalyl chloride. Reaction of the acid chloride with N-methoxy-N-methylamine hydrochloride yields the corresponding substituted N-methoxy-N-methylbenzamide. The desired substituted-phenyl cyclopropyl ketone is then obtained by reacting the benzamide with cyclopropylmagnesium bromide. Aryl cyclopropyl ketones also may be prepared by reacting cyclopropanecarboxylic acid chloride with an appropriately substituted-phenyl compound in the presence of Friedel-Crafts catalyst, e.g., aluminum chloride.

The following examples provide additional details of synthetic methods used to prepare the insecticidal hydrocarbons of this invention. Table 1 lists some of these compounds. Compound numbers shown in the examples are those assigned in this table.

EXAMPLE 1

Synthesis of 1-cyclopropyl-1-(4-Trifluoromethoxyphenyl)-4-(4-Fluoro-3-Phenoxyphenyl)-2-Butene (Compound 6)

Step A Synthesis of 4-trifluoromethoxyphenyl cyclopropyl ketone as an intermediate Under a nitrogen atmosphere, 10% of a solution of 119.0 grams (0.98 mole) of cyclopropyl bromide in 125 mL of tetrahydrofuran was added to a suspension of 25.5 grams (1.03 moles) of magnesium turnings in 300 mL of tetrahydrofuran. The reaction was initiated by warming the reaction mixture to 35° C. Upon initiation of the reaction the remainder of the bromide/tetrahydrofuran solution was added dropwise while maintaining the reaction mixture temperature at 40°–50° C. The complete addition required approximately 90 minutes, after which time the reaction mixture was stirred at 40°–50° C. for an additional 1 hour. The reaction mixture was cooled to 15°–20° C., and 140.0 grams (0.75 mole) of 4-trifluoromethoxybenzonitrile was added dropwise during a 90 minute period. The reaction mixture temperature was maintained at 25° C. or less throughout the addition. Upon completion of the addition the reaction mixture was allowed to return to ambient temperature where it stirred for 18 hours. After this time the reaction mixture was poured into 1000 mL of cold (10° C.) aqueous 2N hydrochloric acid. The mixture was stirred for 1 hour, and then it was extracted with one 1000 mL portion and two 50 mL portions of diethyl ether. The combined extracts were concentrated under reduced pressure to a residue. The residue was redissolved in 2000 mL of diethyl ether, and the solution was washed in turn with two 500 mL portions of aqueous 1N hydrochloric acid, one 500 mL portion of an aqueous solution saturated with sodium bicarbonate, two 500 mL portions of water, and one 300 mL portion of an aqueous solution saturated with sodium chloride. The organic layer was dried with magnesium sulfate and filtered. The filtrate was concentrated under reduced pressure to a residual oil. The oil was distilled under high vacuum yielding 149.7 grams of 4-trifluoromethoxyphenyl cyclopropyl ketone; b.p. 53°–56° C./0.04 mm.

The NMR spectrum was consistent with the proposed structure.

Step B Synthesis of 1-cyclopropyl-1-(4-trifluoromethoxyphenyl)-2-propen-1-ol as an intermediate Under a nitrogen atmosphere a stirred solution of 550 ml (0.55 mole) of 1M vinylmagnesium bromide in tetrahydrofuran was cooled to 10°–15° C., and a solution of 115.0 grams (0.5 mole) of cyclopropyl 4-trifluoromethoxyphenyl ketone in 100 ml of tetrahydrofuran was added dropwise during a 30 minute period. Upon completion of addition the reaction mixture temperature was maintained at less than 20° C. where it was stirred for one hour. The reaction mixture was poured into a mixture of 2000 ml of pH5 buffer in 1000 ml of ice. To this was added 1000 ml of diethyl ether. The mixture was stirred until the ice melted. The aqueous layer was separated and was washed with two 500 ml portions of diethyl ether. The ether washes were combined with the original organic layer, and the combination was washed in turn with two 500 ml portions of the pH5 buffer solution, two 500 ml portions of water, and one 300 ml portion of an aqueous solution saturated with sodium chloride. The organic layer was dried with ground sodium carbonate and filtered. The filtrate was concentrated under reduced pressure yielding 130.0 grams of 1-cyclopropyl-1-(4-trifluoromethoxyphenyl)-2-propen-1-ol.

The NMR spectrum was consistent with the proposed structure.

Step C Synthesis of 3-chloro-1-cyclopropyl-1-(4-trifluoromethoxyphenyl)-1-propene as an intermediate Under a nitrogen atmosphere a solution of 130.0 grams (0.5 mole) of 1-cyclopropyl-1-(4-trifluoromethoxyphenyl)-2-propen-1-ol and 49.3 grams (0.54 mole) of pyridine in 500 mL of methylene chloride was stirred, and 60.2 grams of thionyl chloride was added dropwise during a 30 minute period. The reaction mixture was maintained at 0° to 10° C. throughout the addition. Upon completion of addition the reaction mixture was stirred for 1 hour and then was diluted with 500 mL of methylene chloride and 500 mL of ice. The mixture was stirred until the ice melted. The organic layer was separated and was in turn washed with two 500 mL portions of aqueous 0.5N hydrochloric acid, two 500 mL portions of an aqueous solution saturated with sodium bicarbonate, two 500 mL portions of water, and two 500 mL portions of an aqueous solution saturated with sodium chloride. The organic layer was dried with sodium sulfate and filtered. The filtrate was concentrated under reduced pressure yielding 113.5 grams of 3-chloro-1-cyclopropyl-1-(4-trifluoromethoxyphenyl)-1-propene.

The NMR spectrum was consistent with the proposed structure.

Step D Synthesis of [3-cyclopropyl-3-(4-trifluoromethoxyphenyl)-2-propen-1-yl]triphenylphosphonium chloride as an intermediate A stirred solution of 113.5 grams (0.41 mole) of 3-chloro-1-cyclopropyl-1-(4-trifluoromethoxyphenyl)-1-propene and 113.0 grams (0.43 mole) of triphenylphosphine in 400 mL of toluene was heated at reflux for 4 hours. After this time the reaction mixture was cooled and concentrated under reduced pressure to a residue. The residue was triturated with 1000 mL of diethyl ether. The ether was decanted from the residue, and the residue was triturated with two more 1000 mL portions of diethyl ether in the manner described above. The solid residue was dried under reduced pressure yielding 176.0 grams of [3-cyclopropyl-3-(4-trifluoromethoxyphenyl)-2-propen-1-yl]triphenylphosphonium chloride.

The NMR spectrum was consistent with the proposed structure.

Step E Synthesis of 1-cyclopropyl-1-(4-trifluoromethoxyphenyl)-4-(4-fluoro-3-phenoxyphenyl)-1,3-butadiene as an intermediate Under a nitrogen atmosphere, 14.6 grams (0.36 mole) of sodium hydride (60% in mineral oil) was washed with two 100 mL portions of heptane. The washed sodium hydride was stirred with 350 mL of dimethyl sulfoxide, and the mixture was heated at 50°-55° C. for 3.5 hours until a clear solution formed. The reaction mixture was cooled to 25° C., and a solution of 176.0 grams (0.327 mole) of [3-cyclopropyl-3-(4-trifluoromethoxyphenyl)-2-propen-1-yl]triphenylphosphonium chloride in 300 mL of dimethyl sulfoxide was added in a steady stream. The reaction mixture temperature was maintained at 30° C. or less throughout the addition. Upon completion of addition the reaction mixture was stirred for 30 minutes, and then 69.5 grams (0.323 mole) of 4-fluoro-3-phenoxybenzaldehyde was added in a steady stream during a 15 minute period. The reaction mixture temperature was maintained at 35° during the addition. Upon completion of addition the reaction mixture was stirred for 1 hour and then was poured into a mixture of 2500 mL of aqueous 1N hydrochloric acid in 500 mL of ice. The mixture was stirred until the ice melted and then was extracted with three 1000 mL portions of diethyl ether. The combined extracts were in turn washed with one 1000 mL portion and two 500 mL portions of aqueous 0.5N hydrochloric acid, one 1500 mL portion of an aqueous solution saturated with sodium bicarbonate, two 1000 ml portions of water, and two 500 ml portions of an aqueous solution saturated with sodium chloride. The organic layer was dried with magnesium sulfate and filtered. The filtrate was concentrated under reduced pressure to a residue. The residue was subjected to column chromatography on silica gel. Elution was accomplished using 20% methylene chloride in heptane. The appropriate fractions were combined and concentrated under reduced pressure yielding 112.6 grams of 1-cyclopropyl-1-(4-trifluoromethoxyphenyl)-4-(4-fluoro-3-phenoxyphenyl)-1,3-butadiene.

The NMR spectrum was consistent with the proposed structure.

Step F Synthesis of 1-cyclopropyl-1-(4-trifluoromethoxyphenyl)-4-(4-fluoro-3-phenoxyphenyl)-2-butene (Compound 6)

A stirred mixture of 1.64 grams (0.068 mole) of magnesium turnings in 200 mL of methanol was warmed to reflux, and a solution of 3.0 grams (0.0068 mole) of 1-cyclopropyl-1-(4-trifluoromethoxyphenyl)-4-(4-fluoro-3-phenoxyphenyl)-1,3-butadiene was added dropwise. Upon completion of addition the reaction mixture was heated at reflux for one hour. The reaction mixture was cooled and stirred with ethyl acetate and aqueous 3N hydrochloric acid. The mixture was filtered, the organic layer was separated from the filtrate, and it was washed in turn with aqueous 1N hydrochloric acid and water. The organic layer was dried with magnesium sulfate and filtered. The filtrate was concentrated under reduced pressure yielding 2.5 grams of 1-cyclopropyl-1-(4-trifluoromethoxyphenyl)-4-(4-fluoro-3-phenoxyphenyl)-2-butene.

The NMR spectrum was consistent with the proposed structure.

EXAMPLE 2

Synthesis of
1-Cyclopropyl-1-(4-Chlorophenyl)-4-(4-Fluoro-3-Phenoxyphenyl)-2-Butene (Compound 2)

Step A Synthesis of 1-cyclopropyl-1-(4-chlorophenyl)-2-propen-1-ol as an intermediate This compound was prepared in a manner analogous to that of Example 1, Step B, using 18.1 grams (0.1 mole) of the commercially available 4-chlorophenyl cyclopropyl ketone and 110 mL (0.11 mole) of 1M vinylmagnesium bromide in tetrahydrofuran. The yield of 1-cyclopropyl-1-(4-chlorophenyl)-2-propen-1-ol was 20 grams.

Step B Synthesis of 3-cyclopropyl-3-(4-chlorophenyl)propenal as an intermediate

To a stirred solution of 51.3 grams (0.192 mole) of pyridinium chlorochromate in 210 mL of methylene chloride was added in one portion a solution of 20.0 grams (0.096 mole) of 1-cyclopropyl-1-(4-chlorophenyl)-2-propen-1-ol in 25 mL of methylene chloride. Upon completion of addition the reaction mixture was stirred at ambient temperature for two hours. The supernatent liquid was decanted from a residue, and the residue was extracted with diethyl ether. The decantate and the extract were combined and were washed in turn with two 100 mL portions of aqueous 5% hydrochloric acid, and a 50 mL portion of an aqueous solution saturated with sodium bicarbonate. The organic layer was dried with sodium sulfate and filtered. The filtrate was concentrated under reduced pressure to a residue. The residue was subjected to column chromatography on silica gel using 5% diethyl ether in hexane as the eluant. The appropriate fractions were combined and concentrated under reduced pressure yielding 6.8 grams of 3-cyclopropyl-3-(4-chlorophenyl)propenal.

Step C Synthesis of 4-fluoro-3-phenoxyphenylmethanol chloride as an intermediate To a stirred slurry of 1.4 grams (0.0375 mole) of 95% lithium aluminum hydride in 50 mL of diethyl ether was added dropwise during a one hour period a solution of 21.6 grams (0.1 mole) of 4-fluoro-3-phenoxybenzaldehyde in 50 mL of diethyl ether. Upon completion of addition the reaction mixture was heated at reflux for one hour. The reaction mixture was then cooled to 15° C., and 1.4 mL of water was cautiously added dropwise. Upon completion of addition the reaction mixture was again cooled to 15° C., and sequentially 1.4 mL of aqueous 15% sodium hydroxide and 4.2 mL of water were added. The reaction mixture was filtered through diatomaceous earth, and the filtrate was concentrated under reduced pressure yielding 19.5 grams of 4-fluoro-3-phenoxyphenylmethanol.

Step D Synthesis of 4-fluoro-3-phenoxyphenylmethyl chloride as an intermediate

To a stirred solution of 12.6 grams (0.106 mole) of thionyl chloride and one drop (catalyst) of pyridine in 25 mL of toluene was added dropwise a solution of 19.5 grams (0.088 mole) of 4-fluoro-3-phenoxyphenylmethanol in 30 mL of toluene at such a rate as to maintain the reaction mixture temperature at 25°-35° C. Upon completion of the 45 minute addition time, the reaction mixture was warmed to 45° C. where it was stirred during a one hour period. After this time the reaction mixture was cooled, and the excess thionyl chloride was removed under reduced pressure. The residue, 23.5 grams of a semi-solid mixture, was combined with 114.2 grams of the same material from a previous reaction. The combination was distilled under reduced pressure yielding 100.3 grams of 4-fluoro-3-phenoxyphenylmethyl chloride; b.p. 98°-105° C./0.025-0.055 mm. The nmr spectrum was consistent with the proposed structure.

Step E Synthesis of 4-fluoro-3-phenoxyphenylmethyltriphenylphosphonium chloride as an intermediate A solution of 11.8 grams (0.05 mole) of 4-fluoro--3-phenoxyphenylmethyl chloride and 13.1 grams (0.05 mole) of triphenylphosphine in 150 mL of dry tetrahydrofuran was stirred for 72 hours. After this time the reaction mixture was concentrated under reduced pressure to a residual solid. The residue was stirred with diethyl ether and filtered to collect the solid. The solid was washed repeatedly with diethyl ether and dried yielding 15.0 grams of 4-fluoro-3-phenoxyphenylmethyltriphenylphosphonium chloride.

Step F Synthesis of 1-cyclopropyl-1-(4-chlorophenyl)-4-(4-fluoro-3-phenoxyphenyl)-1,3-butadiene as an intermediate A stirred solution of 0.71 gram (4.4 mL–0.011 mole) of n-butyllithium (2.5M in hexane) in 50 mL of dry tetrahydrofuran was cooled to −78° C., and 4.98 grams (0.01 mole) of 4-fluoro-3-phenoxyphenylmethyltriphenylphosphonium chloride (prepared in Steps C-E) was quickly added. Upon completion of addition the reaction mixture was stirred at −78° C. for one hour, and then a solution of 2.03 grams (0.01 mole) of 3-cyclopropyl-3-(4-chlorophenyl)-2-propenal (prepared in Steps A and B) in 10 mL of dry tetrahydrofuran was added dropwise during a 10 minute period. Upon completion of addition the reaction mixture was stirred at −78° C. for one hour and then was allowed to warm to ambient temperature where it was stirred for two hours. The reaction was quenched with 10 mL of aqueous dilute hydrochloric acid, and the reaction mixture was extracted with diethyl ether. The ether extract was dried with sodium sulfate and filtered. The filtrate was concentrated under reduced pressure to a residue. The residue was subjected to column chromatography on silica gel. Elution was accomplished using 5% ethyl acetate in hexane. The appropriate fractions were combined and concentrated under reduced pressure yielding 1.4 grams of 1-cyclopropyl-1-(4-chlorophenyl)-4-(4-fluoro-3-phenoxyphenyl)-1,3-butadiene. The nmr spectrum was consistent with the proposed structure.

Step G Synthesis of 1-cyclopropyl-1-(4-chlorophenyl)-4-(4-fluoro-3-phenoxyphenyl)-2-butene (Compound 2)

This compound was prepared in a manner analogous to that of Example 1, Step F, using 1.0 gram (0.003 mole) of 1-cyclopropyl-1-(4-chlorophenyl)-4-(4-fluoro-3-phenoxyphenyl)-1,3-butadiene and 0.5 gram (0.020 mole) of magnesium turnings in 30 mL of methanol. The yield of 1-cyclopropyl-1-(4-chlorophenyl)-4-(4-fluoro-3-phenoxyphenyl)-2-butene was 0.18 gram. The nmr spectrum was consistent with the proposed structure.

In the normal use of the insecticidal, pyrethroid-like compounds of the present invention, the compounds usually will not be employed free from admixture or dilution, but ordinarily will be used in a suitable formulated composition compatible with the method of application and comprising an insecticidally effective amount of pyrethroid-like compound. The compounds of this invention, like most pesticidal agents, may be blended with agriculturally acceptable surface-active agents and carriers normally employed for facilitating the dispersion of active ingredients, recognizing the accepted fact that the formulation and mode of application of an insecticide may affect the activity of the material. The pyrethroid-like compounds of this invention may be applied, for example, as sprays, dusts, or granules to the area where pest control is desired. As will be obvious to the skilled artisan, the type of application will vary with the pest and the environment. Thus, the compounds of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the pyrethroid-like compounds. The granule particles are relatively large, typically having a diameter of about 400-2500 microns. The particles are either impregnated with the compounds of this invention from solution or coated with these pyrethroid-like compounds, adhesive sometimes being employed. Granules generally contain 0.05 to 25%, preferably 0.5 to 15%, most preferably 0.5 to 5%, active ingredient as the insecticidally effective amount.

Dusts are admixtures of these pyrethroid-like compounds with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling insects contains 1 part of pyrethroid-like compound and 99 parts of talc.

The compounds of the present invention may be made into liquid concentrates by dissolution or emulsification in suitable liquids and into solid concentrates by admixture with talc, clays, and other solid carriers known or used in the pesticide art. The concentrates are compositions containing, as an insecticidally effective amount, about 5-50% pyrethroid-like compound, and 95-50% inert material, which includes surface-active dispersing, emulsifying, and wetting agents, but even higher concentrations of active ingredient may be employed. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects contains 5 parts of pyrethroid-like compound, 1.5 parts sodium lignosulfonate, 1.5 parts sodium alkylnaphthalene sulfonate, and 92 parts attapulgite clay.

Manufacturing concentrates are useful for shipping low melting compounds of this invention. Such concentrates are prepared by melting the low melting solid compounds together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the pyrethroid-like compound with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfates of higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long chain mercaptans and ethylene oxide. Many other types of useful surface-active agents are available in commerce. The surface-active agent, when used, normally comprises about 1-15% by weight of the insecticidal composition.

Other useful formulations include simple solutions of the active ingredient in a solvent in which it is completely soluble at the desired concentrations, such as acetone or other solvents.

An insecticidally effective amount of pyrethroid-like compounds in an insecticidal composition diluted for application is normally in the range of about 0.001% to about 8% by weight. Many variations of spraying and dusting compositions known in the art may be used by substituting the compounds of this invention into compositions known or apparent in the art.

The insecticidal and acaricidal compositions of this invention may be formulated with other active ingredients, including other insecticides, nematicides, acaricides, fungicides, plant growth regulators, fertilizers, etc. In using the compositions to control insects and acarids, it is only necessary that an insecticidally and acaricidally effective amount of pyrethroid-like compound be applied to the locus where control is desired. Such locus may, e.g., be the insects themselves, plants upon which the insects feed, or the habitat of the insects. When the locus is soil, e.g., soil in which agricultural crops are or will be planted, the active compound may be applied to and optionally incorporated into the soil. For most applications an insecticidally effective amount will be about 75 to 4000 grams per hectare, preferably 150 grams to 3000 grams per hectare.

The insecticidal activity of the pyrethroid-like compounds of this invention as identified in Table 1, appended, was evaluated as follows:

Foliar Evaluation

Compounds within the scope of this invention were tested by foliar application at various concentrations in aqueous solutions containing 10% (volume/volume) acetone and water. Insect species utilized included the cabbage looper (*Trichoplusia ni*), Mexican bean beetle (*Epilachna varivestis*), pea aphid (*Acryrthosiphon pisum*), tobacco budworm (*Heliothis virescens*) and twospotted spider mite (*Tetranychus urticae*).

For all insects except the pea aphid, pinto beans (*Phaseolus vulgaris*) plants were treated with the test solutions. The test solutions were applied with a sprayer to the upper and lower surfaces of the plant leaves to runoff. The plants were then allowed to dry and were severed at the base of the stem before being placed in cups. Ten second instar individuals of the appropriate insect species, except the tobacco budworm, were placed in each cup and the cup covered. Tests with the tobacco budworm used four replicates with each replicate containing five second instar tobacco budworms. In all tests, mortality was read 48 hours later.

In the case of the pea aphid, fava bean (*Vicia faba*) was substituted for pinto bean. The treated, potted plants were placed in cups infested with ten individuals and covered. Mortality was read 48 hours later.

Acaricidal tests were performed using the following procedure: Leaves infested with adult twospotted spider mites (*Tetranvchus urticae*) were removed from culture plants and cut into segments containing 50-75 female mites. Each segment was placed on the upper leaf surface of a whole pinto bean plant. After the mites had migrated to the under surfaces of the leaves, the leaf segments used to infest were removed, and each plant was sprayed with test chemicals as described above. After the plants had dried, the entire plant and pot were placed in metal trays in a hood, a supply of water in the tray keeping the plants turgid. After 48 hours the living and dead mites were counted, and percent mortality was calculated.

The results of these tests are shown in Table 2.

Soil Evaluation

Soil evaluation of insecticidal activity of test compounds were conducted against the southern corn rootworm (Diabrotica undecimounctata Howardi). A 0.25 ml aliquot of a stock solution containing 64 mg of the candidate insecticide in 4.0 ml of acetone was pipetted into 41 mL of distilled water containing 0.1% octylphenoxypolyethoxyethanol emulsifier. The resultant solution had a concentration of 15 ppm and was serially diluted to obtain additional test solutions of 7.5 ppm and 3.25 ppm in concentration. In all cases, four mL of each test solution was pipetted into a 4 ounce specimen cup containing two two-day-old corn sprouts completely covered by 26 grams of dry sandy soil. The treated soil in each cup was allowed to stand uncovered in a hood to evaporate the acetone. Each cup was capped and the soil in each cup was mixed thoroughly. The cap of each cup was removed, and ten second instar southern corn rootworm larvae were added to each cup. The cups were each covered with lids perforated with two small holes to allow for ventilation. The cups were then held under fluorescent light (12 hours light: 12 hours dark) at 24°–26° C. for 48 hours. An untreated check and an appropriate standard were included in each test. Two replicates were run for each chemical treatment. The unaffected larvae from the soil of each cup were extracted by placing the contents of each cup into a modified Berlese polyethylene funnel fitted with an 18-mesh screen. The funnels were placed over containers of an aqueous detergent solution. Incandescent lights (100 watts) were placed 36 cm above the soil in each funnel. The heat from these lights slowly dried the soil causing larvae that had not been affected by the candidate insecticide to emerge from the soil and drop out of the funnel into the detergent solution. The percent mortality was determined by comparing the number of live larvae in the detergent solution with the total number of larvae infested during the initiation of the test. Percent mortality was determined in this manner for each concentration.

Results of these tests are reported in Table 3.

Fish Toxicity

Compounds of the present invention were tested for toxicity to fish using one inch long tilapia (Oreochromis niloticus). Prior to the test the tilapia were acclimated for one week in an aquarium, during which time they were fed with a ration of rice bran and pelletized hog feed. The water in the aquarium was changed daily with distilled water.

Stock solutions of each of the test chemicals were prepared by dissolving the weighed technical material in acetone and adding distilled water to provide a 1% acetone in water solution.

The test solutions were prepared by diluting the appropriate amount of a stock solution to 25 mL with distilled water. The appropriate amount of stock solution was determined for the concentration required in a final volume of 800 mL of test solution. The test chemicals were tested in triplicate at concentrations ranging from 0.005 ppm to 20 ppm. The actual concentrations of the test chemicals needed to determine LC$_{50}$ values were determined by fish toxicity-range of application studies prior to the LC$_{50}$ test. Each 25 mL test chemical solution was added to a one liter aquarium containing 500 mL of 0.01% (v/v) ethylene glycol in water. The aquariums were shaken gently and then allowed to stand for one hour. After this time the tilapia were added by first placing five fish in a container with 275 mL of distilled water and then pouring the water and fish into each aquarium. The dead and live fish were counted after 24 and 48 hours. Any fish observed to be dead was removed from its aquarium immediately. Upon completion of the 48 hour test period, the lethal concentration of each compound tested that would give 50% mortality to the tilapia was determined.

TABLE 1

TABLE OF 2-BUTENE DERIVATIVES

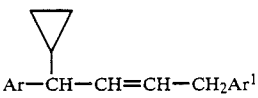

$$Ar-CH-CH=CH-CH_2Ar^1$$

| Cmpd. No. | Ar | Ar$^1$ |
|---|---|---|
| 1 | 4-chlorophenyl | 3-phenoxyphenyl |
| 2 | 4-chlorophenyl | 4-fluoro-3-phenoxyphenyl |
| 3 | 4-trifluoromethylphenyl | 3-phenoxyphenyl |
| 4 | 4-trifluoromethylphenyl | 4-fluoro-3-phenoxyphenyl |
| 5 | 4-trifluoromethoxyphenyl | 3-phenoxyphenyl |
| 6 | 4-trifluoromethoxyphenyl | 4-fluoro-3-phenoxyphenyl |
| 7 | 4-chlorophenyl | 2-methyl[1,1'-biphenyl]-3-yl |
| 8 | 4-cyclopropyl-methoxyphenyl | 2-methyl[1,1'-biphenyl]-3-yl |
| 9 | 4-ethoxyphenyl | 2-methyl[1,1'-biphenyl]-3-yl |
| 10 | 4-methylphenyl | 4-fluoro-3-phenoxyphenyl |
| 11 | 1,3-benzodioxol-5-yl | 3-phenoxyphenyl |
| 12 | 2,2-difluoro-1,3-benzodioxol-5-yl | 2-methyl[1,1'-biphenyl]-3-yl |
| 13 | naphthyl | 4-fluoro-3-phenoxyphenyl |
| 14 | 2,3-dihydro-2,2-dimethyl-benzofuran-5-yl | 4-fluoro-3-phenoxyphenyl |
| 15 | 2,2,3,3-tetrafluoro-benzofuran-5-yl | 2-methyl[1,1'-biphenyl]-3-yl |
| 16 | 2,3-dihydro-2,2-dimethyl-benzofuran-7-yl | 3-phenoxyphenyl |
| 17 | thien-2-yl | 4-fluoro-3-phenoxyphenyl |
| 18 | 4-trifluoromethoxyphenyl | 6-phenoxy-2-pyridyl |
| 19 | 4-difluoromethoxyphenyl | 3-phenoxyphenyl |
| 20 | 3,4-dichlorophenyl | 4-fluoro-3-phenoxyphenyl |
| 21 | phenyl | 4-fluoro-3-phenoxyphenyl |
| 22 | 4-trifluoromethylphenyl | 6-phenoxy-2-pyridyl |
| 23 | 4-methoxyphenyl | 3-phenoxyphenyl |
| 24 | 2,3-dihydro-2,2-dimethyl-benzothien-5-yl | 2-methyl[1,1'-biphenyl]-3-yl |

TABLE 2

FOLIAR INSECTICIDAL AND ACARICIDAL TEST RESULTS

| | Rate | % Kill | | | | |
|---|---|---|---|---|---|---|
| Cmpd No. | (ppm) | CL | MBB | PA | TBW | TSM-S |
| 1 | 100 | 100 | 100 | 75 | 100 | 2 |
| 2 | 100 | 100 | 100 | 80 | 100 | 0 |
| 3 | 100 | 90 | 100 | 45 | 100 | 90 |
| 4 | 100 | 100 | 100 | 90 | 100 | 90 |
| 5 | 100 | 85 | 100 | 100 | 80 | 100 |
| 6 | 100 | 100 | 100 | 85 | 100 | 99 |
| 7 | 500 | 100 | 100 | 60 | 100 | 7 |
| 8 | 500 | 100 | | 5 | 22 | 0 |
| 9 | 1000 | 100 | 90 | 100 | | 100 |

CL = cabbage looper
MBB = Mexican bean beetle
PA = pea aphid
TBW = tobacco budworm
TSM-S = twospotted spider mite (susceptible)

TABLE 3

| SOIL INSECTICIDAL TEST RESULTS | | |
|---|---|---|
| Cmpd No. | Rate (ppm) | Initial % Kill SCR |
| 1 | 7.5 | 45 |
| 2 | 7.5 | 45 |
| 3 | 7.5 | 60 |
| 5 | 7.5 | 50 |
| 6 | 7.5 | 70 |
| 7 | 7.5 | 50 |

SCR = Southern Corn Rootworm

TABLE 4

| Toxicity of Certain 1-cyclopropyl-1,4-diaryl-2-butenes to Fish* | |
|---|---|
| Compound Number | $LC_{50}$ (ppm)** |
| 1 | 3–5 |
| 2 | 7.5–10 |
| 3 | 5–7.5 |
| 5 | 1–3 |
| 6 | 9 |
| cypermethrin | 0.02 |

*Tilapia (*Oreochromis niloticus*)
**The lethal concentration of a compound that will give 50% mortality of a certain species in a normal population

We claim:

1. A compound of the formula

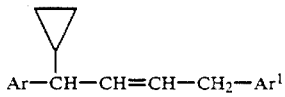

Ar—CH—CH=CH—CH$_2$—Ar$^1$ in which Ar is a substituted or unsubstituted phenyl, naphthyl, or thienyl and Ar$^1$ is a substituted or unsubstituted phenoxyphenyl.

2. A compound of claim 1 in which Ar is a phenyl, naphthyl, or thienyl group which may be substituted by $(C_{1-6})$alkyl, halo, $(C_{1-4})$haloalkyl, $(C_{1-4})$alkoxy, $(C_{1-4})$haloalkoxy, or by a substituent having the structure -A-[C(R$^1$)(R$^2$)]$_n$-A- where R$^1$ and R$^2$ are independently hydrogen, halogen; or $(C_{1-2})$alkyl, n is 1 or 2, and each A is O, S, or CH$_2$ and is bonded to an adjacent carbon atom of the aromatic ring; and Ar$^1$ is phenoxyphenyl optionally substituted with halo or lower alkyl.

3. A compound of claim 2 in which Ar$^1$ is selected from 3-phenoxyphenyl and 4-fluoro-3-phenoxyphenyl and Ar is selected from 4-chlorophenyl, 4-trifluoromethylphenyl and 4-trifluoromethoxyphenyl.

4. A compound of claim 3 in which Ar$^1$ is a 4-fluoro-3-phenoxyphenyl.

5. A compound of claim 4 in which Ar is 4-chlorophenyl.

6. A compound of claim 4 in which Ar is 4-trifluoromethylphenyl.

7. A compound of claim 4 in which Ar is 4-trifluoromethoxyphenyl.

8. An insecticidal or acaricidal composition comprising an insecticidally or acaricidally effective amount of a compound of claim 1 in admixture with one or more compatible agricultural carriers, diluents, adjuvants, or complimentary pesticides.

9. An insecticidal or acaricidal composition comprising an insecticidally or acaricidally effective amount of a compound of claim 2 in admixture with one or more compatible agricultural carriers, diluents, adjuvants, or complimentary pesticides.

10. A method of controlling insects and acarids by applying to the locus where control is desired an insecticidally or acaricidally effective amount of a compound of claim 1.

11. A method of controlling insects and acarids by applying to the locus where control is desired an insecticidally or acaricidally effective amount of a compound of claim 2.

* * * * *

UNITED STATES PATENT AND TRADEMARK OFFICE
CERTIFICATE OF CORRECTION

PATENT NO. : 4,975,451

DATED : December 4, 1990

INVENTOR(S) : Thomas G. Cullen, Scott McN. Sieburth, Gary A. Meier, John F. Engel, Leslie W. Stratton, Alan W. Fritz It is certified that error appears in the above-identified patent and that said Letters Patent is hereby corrected as shown below:

Column 3, lines 46 and 47, "1R,cis-3-(2,2-2-di thylcyclopropanecarboxylic acid;" should read --1R,cis-3-(2,2-dibromoethenyl)-2,2-dimethylcyclocarboxylic acid;--

Signed and Sealed this

Twenty-eighth Day of April, 1992

Attest:

HARRY F. MANBECK, JR.

*Attesting Officer*   *Commissioner of Patents and Trademarks*